(12) United States Patent
Kurtz et al.

(10) Patent No.: US 9,971,004 B2
(45) Date of Patent: May 15, 2018

(54) TREATMENT PLANNING AND DELIVERY USING TEMPERATURE UNCERTAINTY MAPS

(71) Applicant: Profound Medical Inc., Toronto (CA)

(72) Inventors: Ron Kurtz, Oakville (CA); Kee Tang, Caledon (CA); Mathieu Burtnyk, Toronto (CA)

(73) Assignee: Profound Medical, Inc., Mississauga, ON (CA)

( * ) Notice: Subject to any disclaimer, the term of this patent is extended or adjusted under 35 U.S.C. 154(b) by 24 days.

(21) Appl. No.: 14/450,805

(22) Filed: Aug. 4, 2014

(65) Prior Publication Data
US 2015/0038883 A1      Feb. 5, 2015

Related U.S. Application Data

(60) Provisional application No. 61/861,801, filed on Aug. 2, 2013.

(51) Int. Cl.
| | |
|---|---|
| *A61H 1/00* | (2006.01) |
| *G01R 33/48* | (2006.01) |
| *A61B 5/055* | (2006.01) |
| *A61N 7/02* | (2006.01) |
| *G01R 33/28* | (2006.01) |
| *G01R 33/44* | (2006.01) |
| *G06F 3/0484* | (2013.01) |
| *A61B 5/01* | (2006.01) |

(Continued)

(52) U.S. Cl.
CPC ......... *G01R 33/4804* (2013.01); *A61B 5/015* (2013.01); *A61B 5/055* (2013.01); *A61B 5/4381* (2013.01); *A61N 7/02* (2013.01); *A61N 7/022* (2013.01); *G01R 33/285* (2013.01); *G01R 33/443* (2013.01); *G01R 33/4814* (2013.01); *G06F 3/0484* (2013.01); *A61B 2018/00547* (2013.01); *A61B 2018/00636* (2013.01); *A61B 2018/00702* (2013.01); *A61B 2018/00791* (2013.01); *A61B 2090/374* (2016.02); *A61B 2090/3784* (2016.02); *A61N 2007/0004* (2013.01); *A61N 2007/0052* (2013.01); *A61N 2007/0078* (2013.01); *G01R 33/5608* (2013.01)

(58) Field of Classification Search
CPC .................................... A61N 7/02; A61N 7/00
See application file for complete search history.

(56) References Cited

U.S. PATENT DOCUMENTS

| | | |
|---|---|---|
| 787,920 A | 4/1905 | Hofman |
| 4,841,970 A | 6/1989 | Rand |

(Continued)

FOREIGN PATENT DOCUMENTS

WO    WO2013046131 A1    4/2013

OTHER PUBLICATIONS

EPO as ISA, "Extended European Search Report", PCT/IB2014/002321, dated Sep. 12, 2017.

*Primary Examiner* — Hien Nguyen
(74) *Attorney, Agent, or Firm* — Inrinsic Law Group

(57) ABSTRACT

A method and programmable computer system calculates and displays the regions where the temperature can be reliably measured in a thermal therapy procedure. The clinician or automated control system then can make an informed decision to treat these regions or plan a treatment to avoid them based on the sensitivity of surrounding structures to unintended heating.

8 Claims, 5 Drawing Sheets

(51) Int. Cl.
*A61B 5/00* (2006.01)
*A61B 18/00* (2006.01)
*A61N 7/00* (2006.01)
*G01R 33/56* (2006.01)
*A61B 90/00* (2016.01)

(56) References Cited

U.S. PATENT DOCUMENTS

| | | |
|---|---|---|
| 4,844,073 A | 7/1989 | Pohler |
| 5,417,721 A | 5/1995 | Mallasch |
| 5,474,071 A | 12/1995 | Chapelon et al. |
| 5,649,973 A | 7/1997 | Tierney et al. |
| 5,800,485 A | 9/1998 | Trop et al. |
| 6,009,351 A | 12/1999 | Flachman |
| 6,071,238 A | 6/2000 | Chapelon et al. |
| 6,159,207 A | 12/2000 | Yoon |
| 6,517,562 B1 | 2/2003 | Holland |
| RE38,143 E | 6/2003 | Tierney et al. |
| 7,077,858 B2 | 7/2006 | Fletcher et al. |
| 7,101,387 B2 | 9/2006 | Garabedian et al. |
| 7,125,407 B2 | 10/2006 | Edwards et al. |
| 7,243,655 B2 | 7/2007 | Gonzales |
| 7,326,195 B2 | 2/2008 | Willard et al. |
| 7,326,235 B2 | 2/2008 | Edwards |
| 7,344,529 B2 | 3/2008 | Torchia et al. |
| 7,387,638 B2 | 6/2008 | Gonzales |
| 7,480,533 B2 | 1/2009 | Cosman et al. |
| 7,485,109 B2 | 2/2009 | Willard et al. |
| 7,491,223 B2 | 2/2009 | Lasheras |
| 8,311,609 B2 | 11/2012 | Harvey et al. |
| 2002/0010502 A1 | 1/2002 | Tractenberg |
| 2002/0116041 A1 | 8/2002 | Daoud |
| 2003/0069619 A1 | 4/2003 | Fenn et al. |
| 2003/0144593 A1 | 7/2003 | Whitmore et al. |
| 2004/0024434 A1 | 2/2004 | Yang et al. |
| 2005/0065429 A1 | 3/2005 | Zhou |
| 2005/0177209 A1 | 8/2005 | Leung et al. |
| 2006/0142826 A1 | 6/2006 | Willard et al. |
| 2006/0206105 A1* | 9/2006 | Chopra ............... A61B 5/055 606/27 |
| 2007/0106157 A1* | 5/2007 | Kaczkowski ......... A61B 5/015 600/438 |
| 2007/0239062 A1 | 10/2007 | Chopra et al. |
| 2008/0033471 A1 | 2/2008 | Paz et al. |
| 2008/0161785 A1 | 7/2008 | Crowe et al. |
| 2008/0215042 A1 | 9/2008 | Swanson |
| 2009/0018446 A1 | 1/2009 | Medan et al. |
| 2009/0024023 A1* | 1/2009 | Welches ............. A61B 18/201 600/424 |
| 2009/0157070 A1 | 6/2009 | Oskin et al. |
| 2009/0171157 A1 | 7/2009 | Diederich et al. |
| 2011/0178391 A1 | 7/2011 | Fernandez et al. |
| 2011/0319748 A1 | 12/2011 | Bronskill et al. |
| 2012/0101412 A1 | 4/2012 | Vortman et al. |
| 2012/0253097 A1 | 10/2012 | Shohat et al. |
| 2014/0128881 A1* | 5/2014 | Tyc ..................... A61B 18/22 606/130 |

* cited by examiner

TREATMENT PLANNING AND DELIVERY USING TEMPERATURE UNCERTAINTY MAPS

RELATED APPLICATIONS

This application claims the benefit and priority of U.S. Provisional Application 61/861,801, bearing the present title, filed on Aug. 2, 2013, which is hereby incorporated by reference.

TECHNICAL FIELD

This invention relates to treatment planning for delivery of thermal energy to tissue where the treatment uses temperature measurement derived from magnetic resonance imaging (MRI).

BACKGROUND

The use of magnetic resonance imaging (MRI) to obtain temperature related data in a tissue ablation procedure is discussed e.g., in Chopra (U.S. Pat. No. 7,771,418), which is hereby incorporated by reference. Generally, temperature measurements using MRI methods are subject to errors from a variety of sources known to those skilled in the art. When temperature measurements are used as part of a feedback system for thermal energy delivery, these errors contribute to unintended heating or lack of heating of the target region. The present disclosure provides systems and methods for overcoming the effects of and avoiding errors due to such temperature measurement uncertainties. Accordingly, improved accuracy and efficiency of delivery of MRI-guided thermal therapies is made possible. One application for such therapies is in treating the diseased male prostate.

SUMMARY

The method described here calculates and displays the regions where the temperature can be reliably measured. The clinician then can make an informed decision to treat these regions or plan a treatment to avoid them based on the sensitivity of surrounding structures to unintended heating.

In an embodiment, we present a method for delivering thermal therapy to a target volume within a patient comprising collecting and storing data corresponding to a plurality of phase images using a magnetic resonance imaging (MRI) device, generating a reference phase image from said collected plurality of phase images, calculating a temperature uncertainty map in a region of said target volume, and delivering a thermal therapy dose to said target volume determined at least in part by said temperature uncertainty map.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

Figure 1:
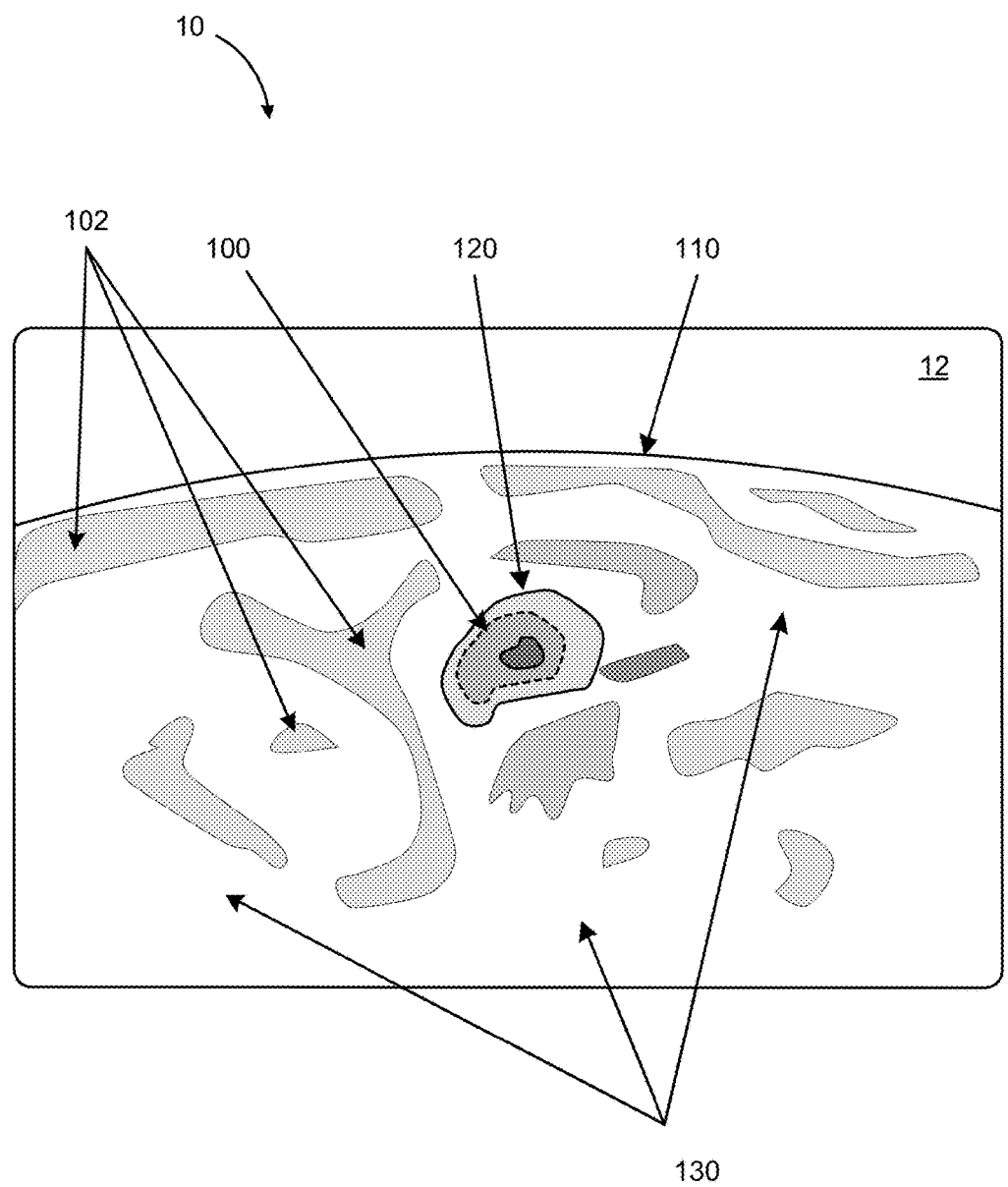
FIG. 1 illustrates a representation of a cross section of a MRI temperature uncertainty map and showing the prostate boundary, target boundary and reference points.

It is useful or necessary to understand the level of precision in image-guided thermal therapy procedures. A visual representation of the precision of the temperature measurement maps (or uncertainty of the same) is therefore a desirable tool in planning and carrying out such procedures. Among other aspects, this invention creates a map of the regions of high temperature uncertainty (or certainty) and displays them to the user during treatment planning as a color map (or any other useful map or representation presenting quantitative data). The user then defines the target boundary of the treatment volume by drawing a contour over the anatomical images such that areas of high temperature uncertainty are avoided. In some aspects, the treatment occurs only in regions where accurate temperature measurement is possible, thus over-heating or under-heating of tissue is avoided. A human user (or a programmed and trained computing machine) can accomplish this step.

The temperature uncertainty (or certainty if the complementary result is desired) is calculated by first collecting a number of complex images (both phase and magnitude), e.g., 25 images, prior to the start of thermal ablative therapy. As per the equation given below, the temperature is calculated as a phase shift, therefore the reference phase is calculated as the average phase over the first 5 images for each pixel. A single initial reference image can suffice, but in this example we assume that several (e.g., five reference images) are used. Those skilled in the art will appreciate that variations on this method for collection of reference images are possible. In another embodiment, phase differences from one image to another are taken, and the phase differences between the successive images are summed to obtain a reference map.

For each of the next 20 (measurement) images the uncorrected temperature is calculated as the difference between the measured phase and the reference phase at each pixel, multiplied by a constant.

Due to drift or temporal changes in the magnetic field, the phase of points at constant temperature will drift. This can be corrected in a number of ways. One such method is to define a number of reference points (e.g., 3 reference points) in the image where the temperature is assumed to remain constant, and to calculate the temperature at these points. The temperature correction at any given point is found by a 2D planar interpolation of the reference points. The reference points may be selected automatically or by an operator. In some aspects, a reference point is chosen because it offers a good signal to noise ratio (SNR). In an example, three such regions or points are chosen, which can be about three pixels on a side if the reference points are small square shaped regions.

A temperature correction as described is then subtracted from the temperature at each pixel of the corresponding measurement image. The base temperature is the subject's core body temperature and is input by the user or measured automatically by a temperature probe. This is added to each pixel to arrive at the absolute temperature. The temperature uncertainty is calculated as the standard deviation of the absolute temperature for each pixel across a plurality (e.g., 20) measurement images. The temperature uncertainty is converted to a color map by assigning each value to a color. For example, shades of blue are assigned to temperature uncertainties below a first threshold value, shades of yellow for values between a second and third threshold values, shades of orange for values between said third and fourth threshold values and purple for values above said fourth threshold value.

Of course the present example is but an illustration of the general method described herein, and those skilled in the art will appreciate similar, equivalent and other useful ways to represent the information and to process it.

Other methods are possible to calculate temperature uncertainty. For example, one can see that the standard deviation is not affected by the choice of base temperature or reference phase; therefore, these steps can be omitted from the above algorithm. It is also possible to use other statistical measures such as the maximum absolute value across the measurement image set, or the z-score. These methods all calculate an uncertainty value over time; therefore, they are considered measures of temporal temperature uncertainty.

In another embodiment the spatial temporal uncertainty can be calculated by using a single image, and for each pixel calculating the standard deviation (or other metric as above) of the neighboring pixels, such as a two dimensional matrix or grid, e.g. a 4×4 grid. It is also possible to use a combination of spatial and temporal images to calculate the temperature uncertainty.

A color map is one possible graphical representation of the temperature uncertainty map. It is also possible to use a gray-scale representation or various shading patterns to denote different values. It is also possible to threshold the temperature uncertainties to show regions that are above or below the threshold value.

This temperature uncertainty map can be displayed on its own or overlaid onto anatomical images to better visualize the locations of high temperature uncertainty. This can be done by making it partially transparent or by making certain values, such as those above or below a threshold transparent.

The temperature uncertainty map can be displayed on multiple image slices simultaneously or one slice at a time. It is also possible to reconstruct and display a 3D model of the temperature uncertainty on its own or overlaid on the anatomical model.

The map of temperature uncertainty can be used to select (automatically or by an operator) reference points in regions of low uncertainty. When the reference points are moved the temperature uncertainty map calculations are redone based on the new reference locations and displayed.

Once the temperature uncertainty map is created the next step is to plan the therapy. This is done by defining target curves, surfaces or volumes, discrete or continuous, which can be drawn by the clinician or calculated by a computer algorithm and displayed on the map. The target may be highlighted in places where the corresponding temperature uncertainty exceeds a threshold or exceeds a temperature measurement used as feedback from the system to its operator or automated controller. The target is then modified to avoid areas of high temperature uncertainty, especially close to critical structures that may otherwise be damaged by over-heating.

In the case of transurethral ultrasound therapy of the prostate, the target is defined as a series of closed curves, one on each axial slice near the prostate boundary. The control point for thermal therapy is the point of intersection of the beam emanating from the transducer in the urethra and the target boundary. The temperature uncertainty is plotted on a graph versus angle for each slice. This allows the clinician to quickly determine the point at which the temperature uncertainty exceeds a threshold.

Another possibility is to calculate and display the targeting error, which is a function of temperature uncertainty, tissue parameters (absorption, conduction, and perfusion), positioning and power delivery errors. In one method the targeting error is calculated by simulating the treatment delivery using the bio-heat transfer equation.

When delivering thermal therapy the temperature images are used to control the ultrasound intensity, frequency and the applicator rate of rotation to provide conformal thermal therapy to the target region. During this time the temperature uncertainty may change if there is motion of the tissue which may result in unintentional heating and damage to untargeted structures. This risk can be mitigated by monitoring the temperature uncertainty for regions that have not been heated, such as those at least a certain angle, e.g., 15 degrees, ahead of the beam direction or those that have cooled back to body temperature. In some aspects, the temperature uncertainty is calculated spatially for some or all points along the target boundary and updated, periodically or from time to time or as desired, as new images are acquired in real-time. In an embodiment, the temperature uncertainty is calculated on said boundary or any points that are used by the operator or controller to control the treatment process.

In an aspect, should the temperature uncertainty ahead of the beam exceed a certain threshold then the operator can be alerted to modify or stop the planned treatment. Alternatively, the software can automatically modify the treatment plan or stop treatment.

FIG. 1 illustrates a cross sectional view taken using an imaging modality such as MRI imaging of a portion of a patient's body in the vicinity of a treatment target volume. The scene shown includes for example a visual output device such as a computer monitor screen 10 or application window of a computer application program for displaying an image 12. The surface of the patient's body (e.g., the surface of his abdomen) is shown at 110 while various zones 102 in the patient's body are shown by a visual representation of their temperatures and/or temperature uncertainties within image 12. The zones 102 can be displayed on screen 10 as colored contours, contour plots, gray scale intensities or other visual representations of the temperature uncertainty. The values plotted and represented are determined as described below.

The image 12 shows a boundary of a target volume such as a male prostate or portion thereof 120. This is an outline on image 12, which can be computer-drawn or drawn with the assistance of an operator on the screen 10. A treatment target boundary 100 is further shown on the image 12, which can be a contour of another color, a dashed contour, or other representation. The target boundary 100 is the intended boundary within which the energy of the thermal treatment process is substantially controlled to a set-point temperature (or thermal dose) ensuring rapid and sufficient cell death of diseased cells within the interior of the volume defined by the target boundary 100. Heat can be conducted outside the target boundary 100 out to the boundary of the prostate 120, which can be measured and controlled to achieve appropriate thermal therapy while reasonably avoiding damage to non-diseased tissues and organs proximal to said diseased locations. Tissues and organs outside the target boundary, even if heated, will not exceed lethal thermal dose or temperature limits.

Methods for determining and controlling the intensity of the thermal therapy treatment as a function of the temperature or desired temperature at such a boundary 100 are described by the present inventors in publications and patent applications available to the public, which are hereby incorporated by reference.

Furthermore, image 12 shows a plurality of exemplary reference points 130, which will be described in more detail below. In all, FIG. 1 thus shows a temperature uncertainty map. Three-dimensional representations of the same can be constructed from additional layers, slices or cross-sectional views like that shown in FIG. 1. The methods described herein can therefore be generalized to three dimensional space by stacking slices such as shown in FIG. 1 side by side to form a 3D volume without loss of generality.

Figure 2:
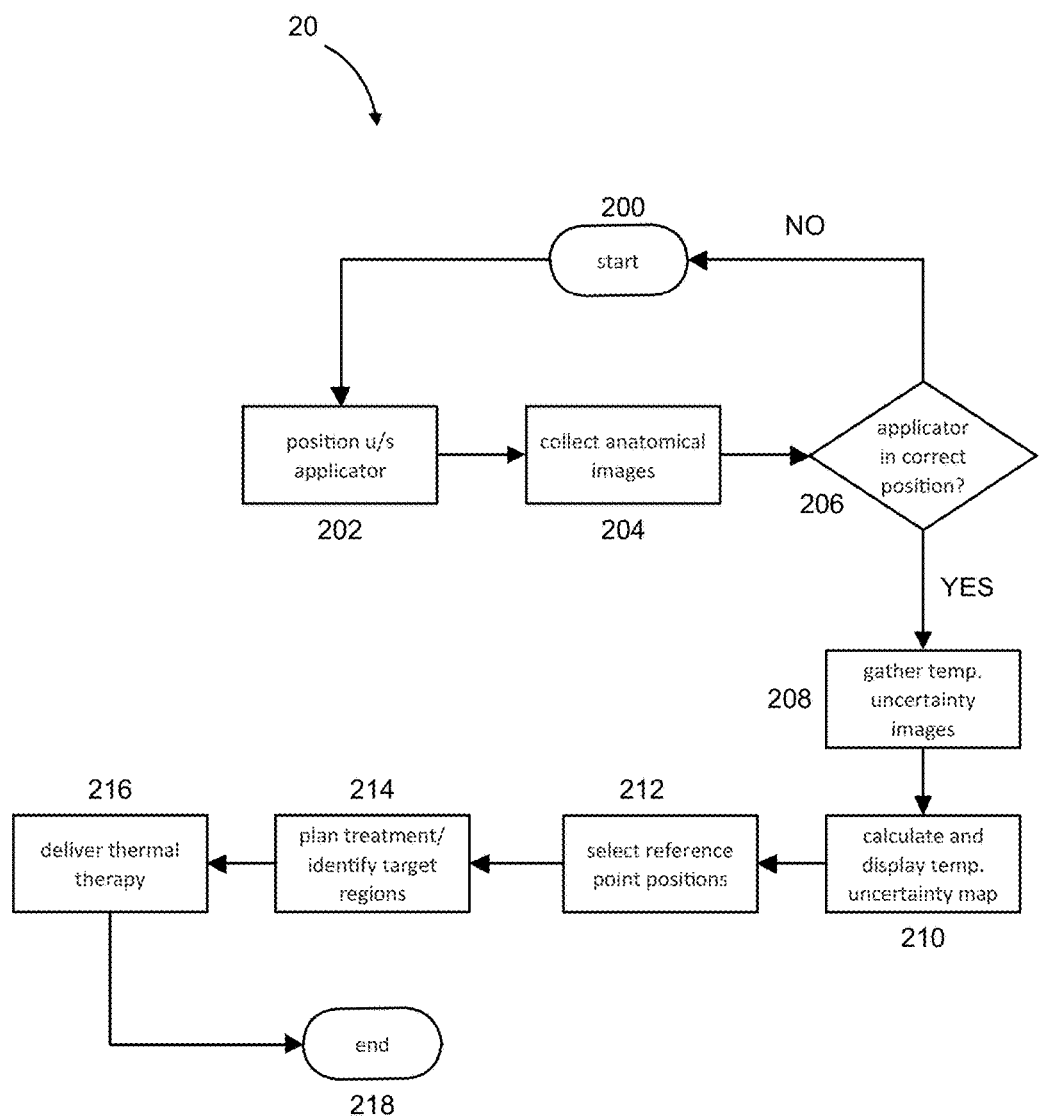
FIG. 2 illustrates an exemplary treatment workflow process.

FIG. 2 illustrates an exemplary process 20 enabling thermal treatment in a MRI-guided environment and accounting for temperature uncertainty in the MRI thermometry portion of the process. The process starts at 200 and an automated or operator-driven positioning of the thermal therapy device in or on the patient is done at step 202. In an example, an ultrasound (u/s) thermal therapy applicator is inserted trans-urethrally into a diseased male prostate organ and positioned so as to deliver thermal therapy to the diseased organ. In another aspect, the patient is placed in a MRI imaging volume or machine bore and temperature scans using MRI thermometry are obtained, slice by slice, through a target region to generate thermal imagery and/or temperature uncertainty maps of the target region.

Anatomical images of the patient or portion of the patient in the vicinity of the target region are obtained at step 204. The system can automatically or semi-automatically determine whether the thermal therapy applicator is in the correct position to deliver the desired thermal therapy to the target region at 206. If not, the process returns to position the thermal therapy applicator at 202.

Once the thermal therapy applicator device is in the correct position, temperature uncertainty images like those depicted in FIG. 1 are collected at 208. A memory or digital storage apparatus can be used to store the data so collected for analysis or other purposes.

The system next calculates and displays the temperature uncertainty maps as depicted above at step 210. These are preferably output to a computer output or display device such as a computer workstation monitor connected to the imaging and therapy device in an overall thermal therapy control system.

A plurality of reference points 130 in the collected slice of temperature uncertainty map 10 are selected or determined at step 212.

Using the temperature data, temperature uncertainty maps and reference points selected, a thermal therapy treatment plan is determined and target points or regions are identified at step 214.

The thermal therapy itself is delivered from a thermal therapy applicator, e.g., an ultrasound transducer array device in or proximal to the desired target region at step 216.

Once the thermal therapy procedure is complete the system or operator terminates the process 20 at 218.

Figure 3:
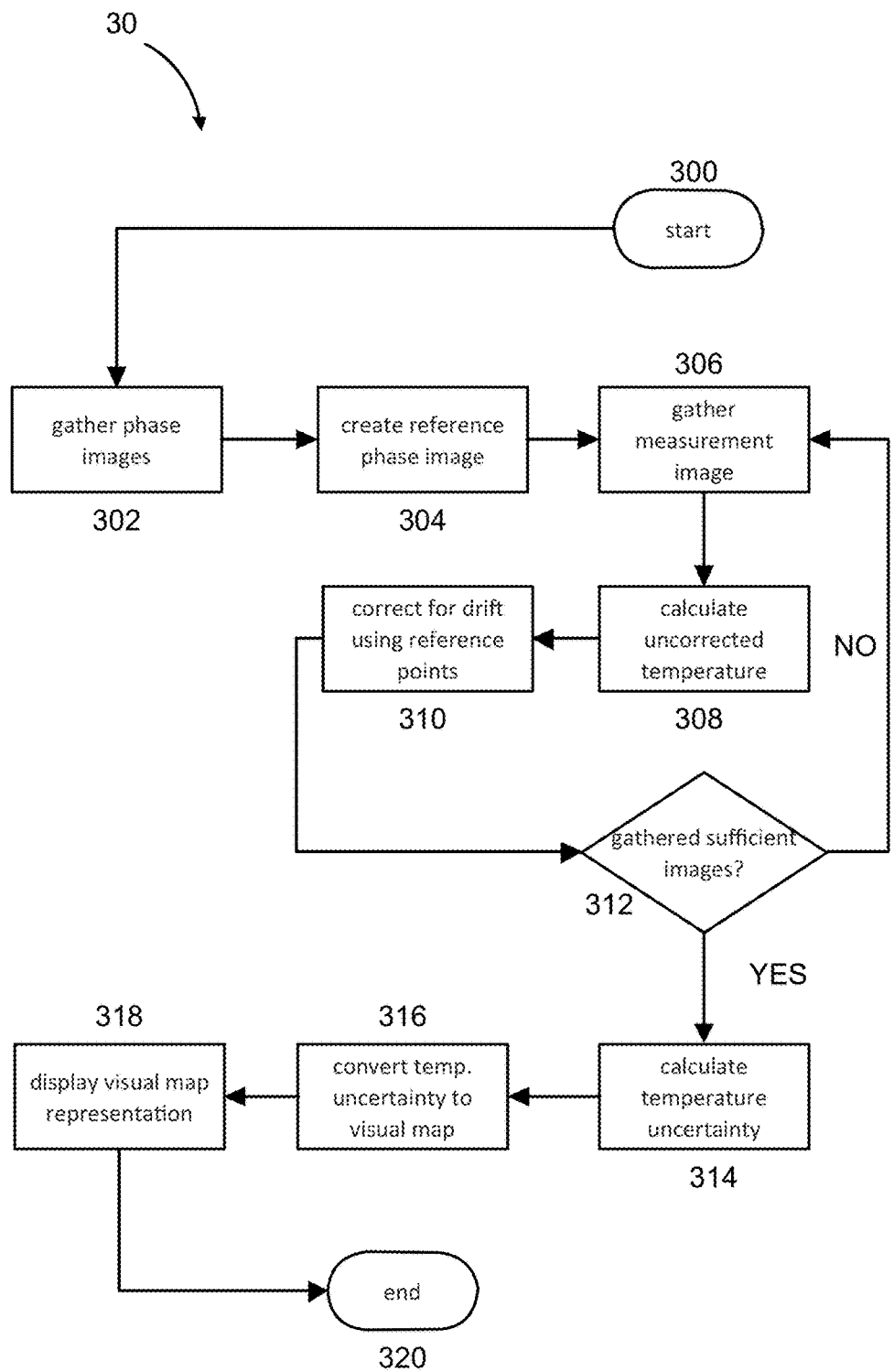
FIG. 3 illustrates an exemplary process for calculating a temperature uncertainty map.

FIG. 3 illustrates another set of steps in an exemplary method 30 for gathering images in the context of image-guided thermal therapy, making appropriate corrections and generating outputs for use in that context.

The process starts at 300 and one or more phase images are gathered from a nuclear magnetic resonance or MRI device in which a patient is placed. In an embodiment, several (e.g., three to ten) phase images are gathered at step 302 and stored in a machine-readable storage device such as a computer memory device. The MRI device can be configured, arranged, programmed and operated so as to run a sequence to output the magnitude and phase images in real time. The output images are output through a signal connection or network connection as desired, for example to another computer device, coupled to the MRI device, where subsequent computations and processing of the MRI data can be carried out.

In an example, an EPI sequence is used to gather the channel uncombined phase images. Other sequences can be used as would be understood by those skilled in the art, for example a GRE sequence.

In some thermal therapies using an ultrasound transducer system, multiple ultrasound transducer elements are deployed in an ultrasonic array placed within the diseased tissue volume. For multi-transducer ultrasound therapy systems, multiple image slices can be taken such that one image slice is taken per ultrasound transducer per therapy applicator system. In yet another aspect, a monitoring slice image can be taken at either end of the imaging slices for full monitoring. The sequence is set in an embodiment to automatically repeat so that stacks of phase images are generated continuously throughout the thermal therapy treatment.

A reference phase image is created at step 304 using data from the gathered phase images in the previous step. This reference phase image is the phase image prior to initiating heating from the thermal therapy procedure. To increase signal to noise, the reference phase image is calculated as the average phase over several (e.g., 5) reference images for each pixel in the image.

A measurement image is collected at step 306. The system then calculates uncorrected temperatures at step 308. In an example, a weighted sum of the phase differences across all channels is calculated and scaled so as to determine temperatures. In an aspect, an MRI device can be programmed to output the combined phase for all coils. In this case the system only requires to calculate the phase difference from the reference image to be scaled to output the temperature in a region of interest.

At step 310 the system corrects for drift using the reference points described earlier. As mentioned before, the drift could be due to temporal changes or drift in the main $B_0$ magnetic field of the MRI machine. A very slow decrease in $B_0$ strength caused by small resistive or other losses in the main magnet solenoid can cause such drift or contribute to the drift. Other causes could include changes in the gradient fields of the MRI system as well. The drift could result in erroneous (typically lower) temperature measurements if not corrected for. Therefore, according to a present aspect, we correct for such drift effects at one or more reference points or areas of the image. The temperature at the reference points is assumed to be that of the patient's body's core temperature, which substantially does not change throughout a therapy treatment. A two-dimensional linear interpolation of the drift is calculated for each measurement slice image and added to the temperature at each pixel in the image to generate a drift-corrected temperature image.

Now the system determines whether sufficient images have been gathered at step 312. If an insufficient number of images were gathered, the process returns to step 306 to gather further imagery. If sufficient images have been gathered, the system calculates the temperature uncertainty at step 314. The temperature uncertainty data is mapped to a visual map at step 316. The visual temperature uncertainty map can take many forms, but in some examples includes contour maps, color maps or similar visual output depicting quantitative temperature uncertainty in space in the region of interest to be treated by the thermal therapy. Such maps are placed into a visual output for display on a screen, printout or other output device at step 318. The process is complete at 320.

Figure 4:
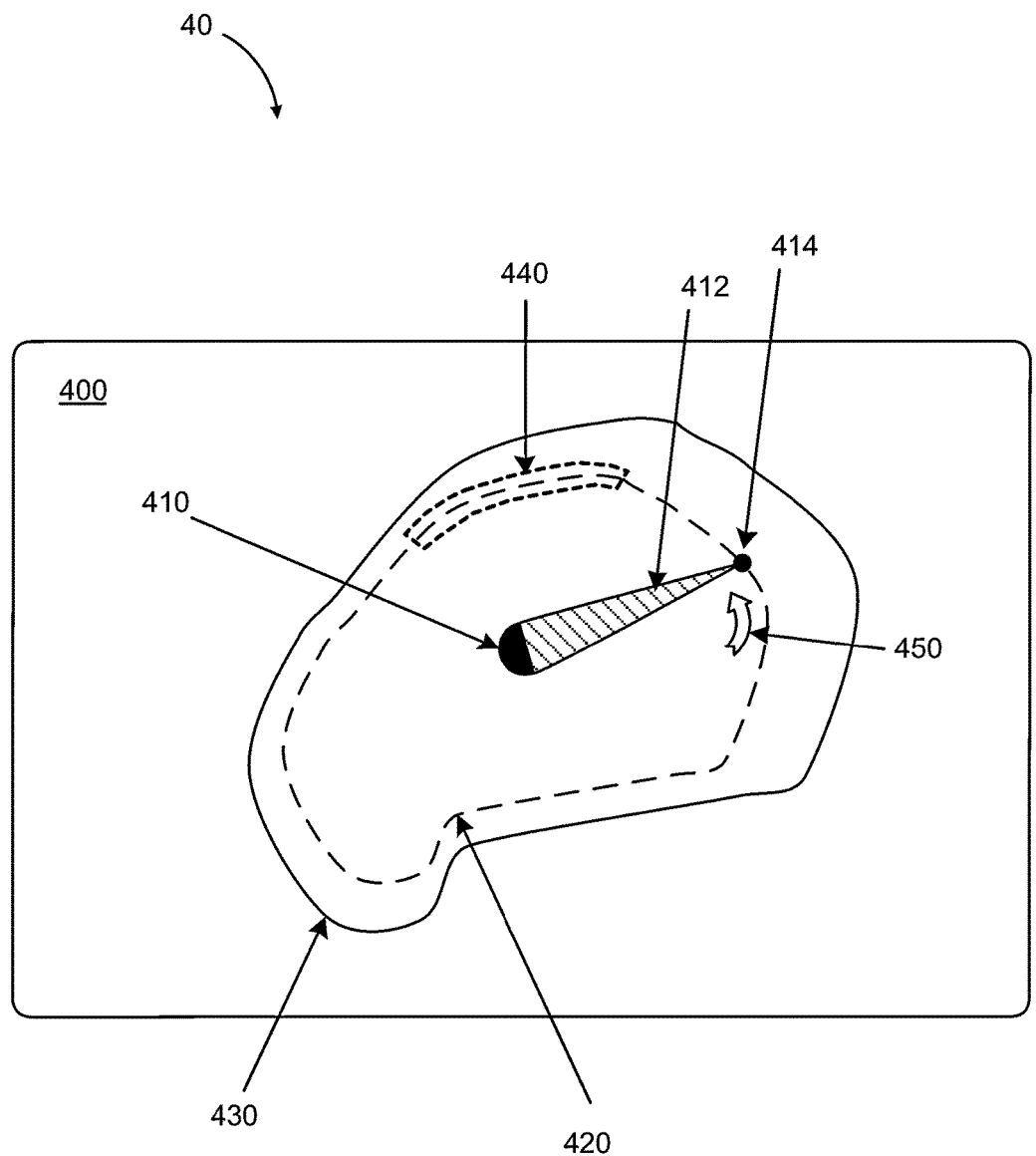
FIG. 4 illustrates a cross section of a rotating thermal therapy device applying energy to a computed contour in a treatment target volume.

FIG. 4 illustrates an axial slice 40 of the treatment volume (e.g., in the prostate organ). The slice can be represented graphically as an image 400 on a computer screen for analysis, or numerically in a machine-readable format for analysis or processing by a computer system. The prostate boundary is represented by contour 430. Within that, a target boundary 420 is defined and can be represented by some other color or line type so that a human operator can see the organ and the target boundaries on a screen simultaneously.

Image 400 also shows the location of the thermal therapy applicator, for example an ultrasound transducer array thermal applicator device 410. Such a device can be within the diseased volume of the prostate, and may be elongated where the current view depicts it in cross section only. The thermal therapy applicator delivers a beam of energy (e.g., ultrasonic energy) along a beam 412 having a nominal direction. Of course, this scenario can be generalized to beams of other shapes or to treatment devices simultaneously emitting more than one treatment beam towards more than one respective direction.

Treatment beam 412 can be rotated about the axis of the treatment device 410 so that treatment beam 412 sweeps around the diseased volume of the prostate and creates heat therein so as to cause a desired clinical effect (e.g., cause cell death). The beam 412 has a general width and length defining the depth or distance to which it delivers effective treatment energy, and the beam 412 meets the target boundary 420 at a characteristic point 414 (without limiting the point to a certain size or shape for the present purpose). Therefore, as the beam 412 is controlled by the movement of the therapy device 410 it sweeps about the angular positions (represented by arrow 450) within the target region of the prostate, at a desired angular rotation speed and power or intensity level, to create a conformal thermal therapy zone. The conformal thermal therapy will be effective in the illustrated slice 40 and also in other axial slices depending on the design and control of the thermal therapy device and the treatment plan.

A portion 440 of the target boundary 420 may be identified as having a high temperature uncertainty level. The portion 440 in other embodiments could be substituted by any other portions of the target boundary 420 or pixels inside or outside the target volume if they are used for monitoring or for control of the thermal treatment process. This can be programmed so that it is indicated to a human or machine operator of the thermal therapy system. Also, the temperature uncertainty as a function of the angular position about the axis of device 410 can be recorded and/or displayed. In this example, the portion 440 exceeds a pre-determined threshold temperature uncertainty, and is colored or highlighted in a fashion to assist in the overall operation of the system and treatment of the patient safely, without exceeding thermal limits to any region of the patient, especially outside the target boundary.

Figure 5:
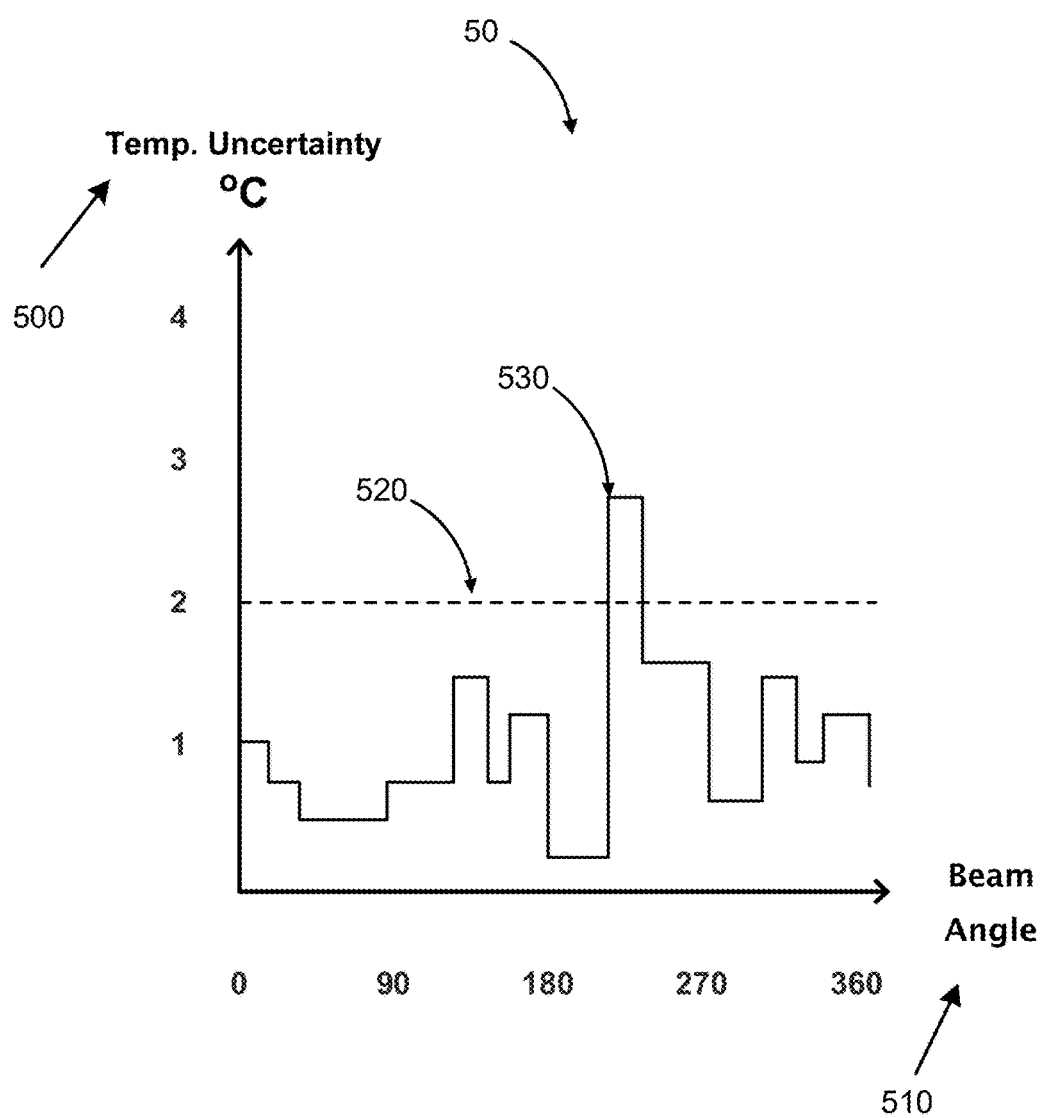
FIG. 5 illustrates an exemplary slice of data showing temperature uncertainty as a function of therapy beam angle for an axial slice of the treatment volume.

FIG. 5 shown an exemplary plot 50 of temperature uncertainty 500 as a function of angular position or beam angle 510 in the above example. A threshold uncertainty 520 can be set and any temperature uncertainty above said threshold (e.g., portion 530) can be programmed to cause an alarm output signal, visual representation on a temperature map or temperature uncertainty map, or similar output. Such slices of data can be analyzed and output, stored or used for control purposes in the context of a thermal therapy procedure.

Although this invention is discussed as it applies to planning and delivery of MRI-guided ultrasound thermal treatment of the prostate, the invention applies to methods of temperature measurement other than MRI, sources of thermal energy other than ultrasound and tissues other than prostate.

One technique used to measure temperature that can be used in this context relies on the proton resonance frequency (PRF) shift which is known to vary with temperature according to the formula:

$$T = \Delta\emptyset / (2\pi * \alpha * Bo * \gamma * TE) + \text{BaseTemp}$$

where T=temperature in degrees, $\Delta\emptyset$=phase difference, $\alpha$=thermal shift coefficient (ppm/° C.), Bo=magnetic field strength (Tesla), $\gamma$=gyromagnetic ratio for H+ nuclei (MHz/Tesla), TE=echo time (sec), BaseTemp=base temperature.

Since the thermometry formula is based on the PRF-sensitivity of water content in tissues, lipid and bone tissues produce unreliable temperature measurements which can be excluded from the thermometry region of interest when making temperature-based decisions.

The method depicted in FIG. 3 can deliver, in some aspects, a visual output like that shown in simplified FIG. 1. As would be appreciated by those skilled in the art, the visual output depicted would be optionally delivered as a contour map, a colored pixelated map depicting temperature uncertainty (or certainty) levels, or other output formats.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for delivering thermal therapy to a target volume within a patient's body, comprising:
   determining a target volume for delivery of thermal therapy thereto;
   in a computer, storing a plurality of phase images captured using a magnetic resonance imaging (MRI) device;
   in said computer, creating a reference phase image of a portion of said patient's body using data corresponding to the plurality of phase images captured using said MRI device, wherein each phase image used in creating the reference phase image comprises a plurality of pixels, each pixel having a corresponding phase, and said reference phase image is created by calculating an average phase over several reference images for each pixel in the phase image;
   in said computer, creating at least one measurement image of said portion of said patient's body using data corresponding to one or more of said phase images captured using said MRI device;
   in a computer, generating at least one uncorrected temperature of the portion of said patient's body using said at least one measurement image and said reference phase image, wherein said at least uncorrected temperature is uncorrected for a phase drift;
   using said computer, correcting for said phase drift in at least one temperature map, such that said temperature map includes corrected temperatures;

using said computer, calculating a temperature uncertainty map in a region of said target volume using said at least one temperature map of said corrected temperatures;

using said computer, determining a treatment plan based at least in part on said temperature uncertainty map; and using a thermal therapy applicator comprising an ultrasound transducer array, delivering a thermal therapy dose to said target volume according to said treatment plan, wherein said treatment plan avoids a region in said target volume having a temperature uncertainty above a temperature uncertainty threshold.

2. The method of claim 1, further comprising, using said computer, determining a plurality of reference points in said temperature uncertainty map.

3. The method of claim 1, further comprising, using said computer, generating an output image corresponding to said temperature uncertainty map and displaying said output image of said temperature uncertainty map.

4. The method of claim 1, further comprising, using said computer, indicating any portions of said temperature uncertainty map that exceed said temperature uncertainty threshold.

5. The method of claim 4, further comprising, using said computer, generating an output signal depending at least in part on whether a portion of the target volume being treated is at a location where said temperature uncertainty threshold has been exceeded.

6. The method of claim 1, further comprising, using said computer, calculating a weighted sum of phase differences across all channels and scaling said weighted sum so as to determine temperatures in slices corresponding to said channels.

7. The method of claim 1, wherein calculating the temperature uncertainty map comprises calculating a standard deviation of the corrected temperatures for each pixel across a plurality of measurement images.

8. The method of claim 7, wherein each uncorrected temperature in each said measurement image is generated by calculating a difference between a measured phase and a reference phase at each pixel, multiplied by a constant.

* * * * *